United States Patent
Di Fabrizio et al.

(10) Patent No.: US 8,749,777 B2
(45) Date of Patent: Jun. 10, 2014

(54) CONCENTRATOR AND LOCATOR DEVICE OF A SOLUTE AND METHOD FOR CONCENTRATING AND LOCATING A SOLUTE

(75) Inventors: Enzo Mario Di Fabrizio, Rome (IT); Giovanni Cuda, Catanzaro (IT); Federico Mecarini, Viterbo (IT); Francesco De Angelis, Rome (IT); Francesco Gentile, Cosenza (IT)

(73) Assignee: Calmed S.r.l., Catanzaro (IT)

( * ) Notice: Subject to any disclaimer, the term of this patent is extended or adjusted under 35 U.S.C. 154(b) by 61 days.

(21) Appl. No.: 13/061,457

(22) PCT Filed: Aug. 28, 2009

(86) PCT No.: PCT/IB2009/053763
§ 371 (c)(1),
(2), (4) Date: Feb. 28, 2011

(87) PCT Pub. No.: WO2010/023635
PCT Pub. Date: Mar. 4, 2010

(65) Prior Publication Data
US 2011/0188037 A1 Aug. 4, 2011

(30) Foreign Application Priority Data
Aug. 29, 2008 (IT) .............. TO2008A0646

(51) Int. Cl.
*G01J 3/44* (2006.01)
(52) U.S. Cl.
USPC ...................................... 356/301
(58) Field of Classification Search
CPC ............ G01N 21/554; B01L 3/502746; B01L 3/5088; B82Y 30/00
USPC .......... 356/301–334; 436/164–172, 524, 525; 422/82.11; 977/857
See application file for complete search history.

(56) References Cited

U.S. PATENT DOCUMENTS

| | | | |
|---|---|---|---|
| 2001/0036674 A1* | 11/2001 | Indermuhle et al. | 436/518 |
| 2005/0239211 A1* | 10/2005 | Uchihara et al. | 436/171 |
| 2005/0275837 A1* | 12/2005 | Zhang et al. | 356/301 |
| 2007/0054416 A1* | 3/2007 | Regnier et al. | 436/518 |
| 2007/0115469 A1 | 5/2007 | Ebstein | |
| 2010/0028604 A1* | 2/2010 | Bhushan et al. | 428/156 |

FOREIGN PATENT DOCUMENTS

EP 1 582 855 A2 10/2005

OTHER PUBLICATIONS

Roach et al. "Progress in superhydrophobic surface development", Soft Matter, 2008, 224-240, Oct. 30, 2007.*
Roach, P. et al.: "Progess in superhydrophobic surface development", Soft Matter, vol. 4, Oct. 30, 2007, pp. 224-240.
McHale, G. et al., "Analysis of Droplet Evaporation on a Superhydrophobic Surface", Langmuir, vol. 21, Sep. 10, 2005, pp. 11053-11060.
International Search Report and Written Opinion for PCT/IB2009/05376309, 2009.

* cited by examiner

*Primary Examiner* — Gregory J Toatley
*Assistant Examiner* — Dominic J Bologna
(74) *Attorney, Agent, or Firm* — Venable LLP; Robert S. Babayi

(57) ABSTRACT

Concentrator and locator device (1) of a solute comprising a substrate (2) and a plurality of prismatic lithographic microstructures (4) orthogonally emerging from the substrate (2). The microstructures (4) are spaced from one another in a periodical manner so as to make such a substrate (2) superhydrophobic.

17 Claims, 2 Drawing Sheets

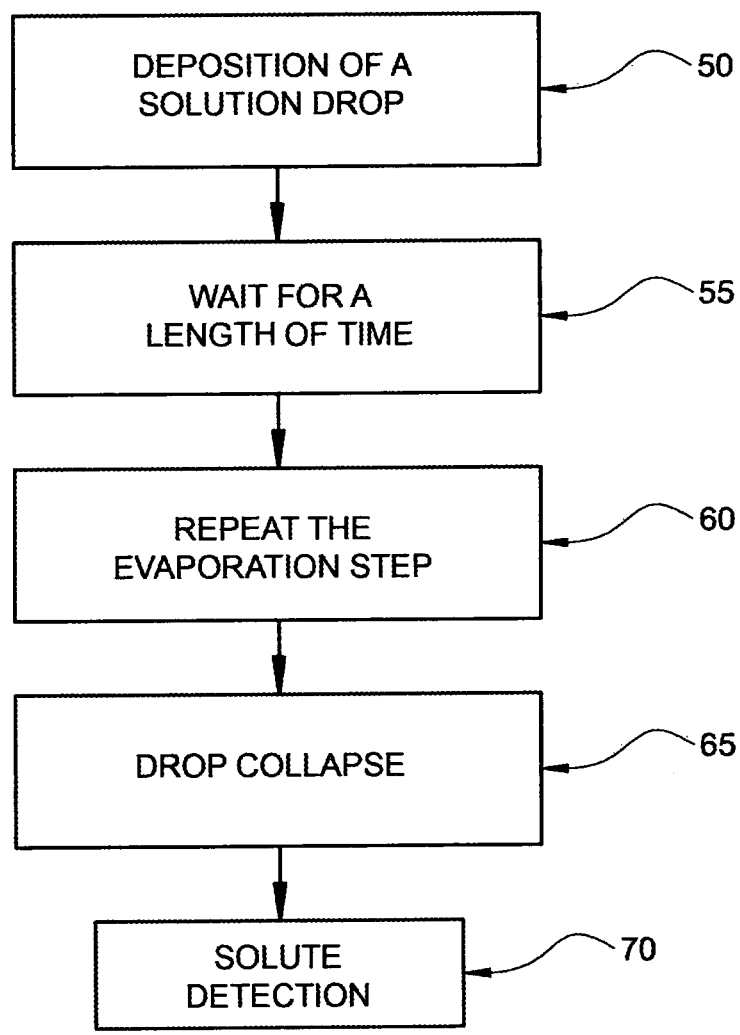

CONCENTRATOR AND LOCATOR DEVICE OF A SOLUTE AND METHOD FOR CONCENTRATING AND LOCATING A SOLUTE

CROSS-REFERENCE TO RELATED APPLICATIONS

This application is a U.S. National Stage Application of PCT/IB009/053763, filed Aug. 28, 2009, which designates the United States and claims the priority of Italian Patent Application No. TO2008A000646, filed on Aug. 29, 2008.

BACKGROUND

1. Field of Invention

The present invention refers to a concentrator and locator device of a solute and to a method for concentrating and locating a solute present in a solution.

2. Related Art

Micro-structured surfaces are known having a geometry such as to reproduce the behaviour of lotus leaves, so as to exploit the known "Lotus Effect".

Lotus leaves display a particular behaviour when they are wet by a liquid; the liquid forms into distinct droplets due to the micrometric corrugation of such surfaces. Such a milimetric corrugation creates high contact angles at the water—leaf surface—air interface. Consequently, the liquid tends to slide off from the surface without dampening it due to a reduced adhesion at the surface itself.

These surfaces are therefore typically used as self-cleaning surfaces since they have a hydrophobic behaviour.

It is often required to identify a solute present inside the solution. This is typically carried out by using, for example, optical devices based on UV (Ultraviolet) absorption, dynamic light scattering, infrared spectroscopes or devices which exploit chemical properties such as liquid or gas phase chromatography.

However, such devices have the drawback that, when the solution is very diluted, it is difficult to locate the solute, and it is thus necessary to perform an analysis on the entire solution, taking a long time before being able to identify the desired substance.

SUMMARY

The purpose of the present invention is therefore that of proposing a concentrator and locator device of a solute and a method for concentrating and locating a solute in a small region of space, so as to allow the solute itself to be rapidly identified.

Briefly, the device according to an embodiment of the invention exploits the high contact angle which is formed between the surface of the device and the solute placed on it, and the super-hydrophobicity of such a surface, to detect, exploiting the principle of evaporation, molecules diluted in the solute up to attomolar ($10^{-18}$ mols/liter) concentrations.

BRIEF DESCRIPTION OF THE DRAWINGS

Further characteristics and advantages of embodiments of the invention shall become clear in the following detailed description, carried out purely as non-limiting example, with reference to the attached drawings, in which:

FIG. 2 is a flow diagram of the operations according to the method of an embodiment of the invention.

DETAILED DESCRIPTION

Figure 1:
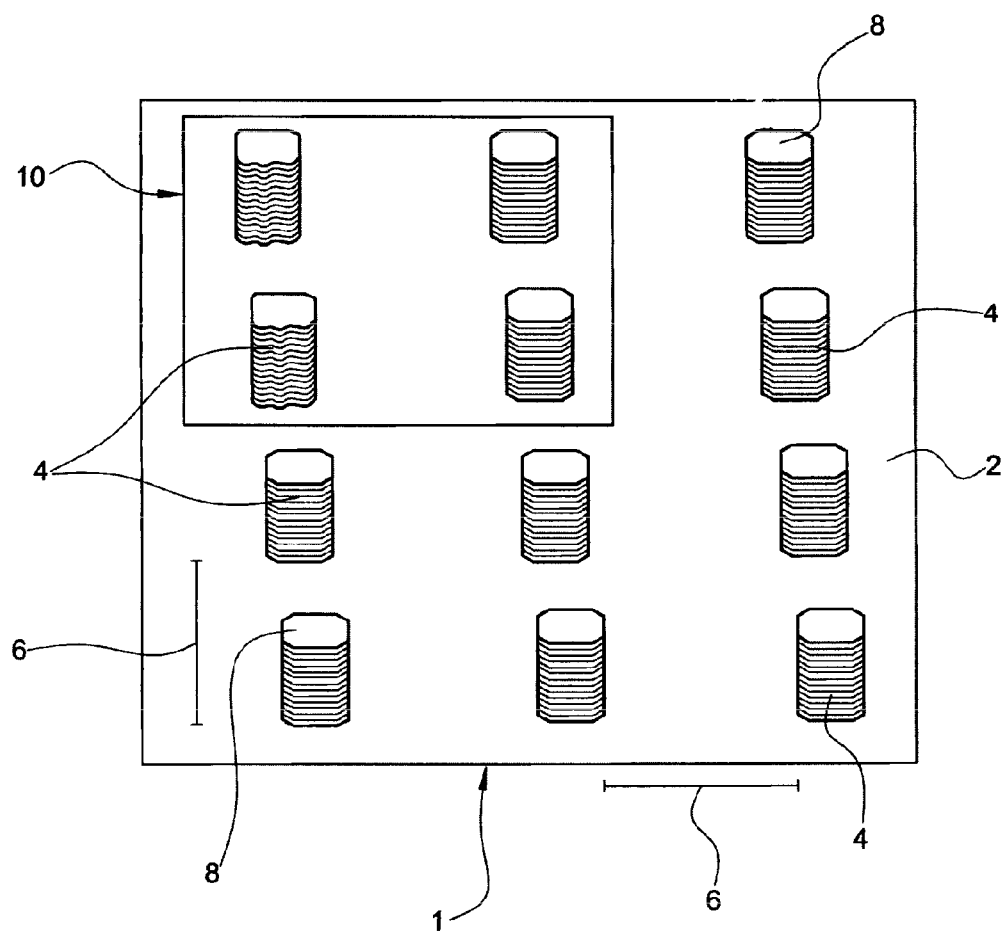
FIG. 1 is a top view of a device according to an embodiment of the invention.

In FIG. 1 a device according to an embodiment of the invention is wholly indicated with reference numeral 1. Such a device 1 comprises a substrate 2, for example silicon or a photopolymer or glass, on which there are prismatic lithographic microstructures 4, preferably having the shape of a parallelepiped, with a shape ratio (the ratio between the height of the parallelepiped and the area of the base) which is greater than a predetermined value T, for example 20. Such microstructures 4 are arranged orthogonally at the surface of the substrate 2, and they are periodically spaced from each other at a predetermined distance 6, comprised in the range 20-50 µm, and they have a base area comprised in the range 1-10 µm.

The microstructures 4, made for example from silicon or from photopolymers, are obtained through per se known deposition or lithography and attack processes.

The substrate 2 becomes super-hydrophobic thanks to the presence of such periodic micro-structures 4.

In a first variant of the invention, on the top 8 of the microstructures 4 an electroless deposition of noble metals is carried out, like for example silver or gold. An oxidation-reduction reaction of the noble metals is obtained which creates a continuous corrugated film of silver or gold on the top 8 of the microstructures 4.

In a second and third variant of the invention, nano-structures are formed on the top 8 of each lithographic microstructure 4.

In particular, in the second variant of the invention a combination of high resolution electron beam lithography and electroless deposition of noble metals such as silver or gold is made. A reaction of oxidation-reduction of the noble metals is made which creates on the top 8 of the microstructures 4 a matrix shaped sub-frame making a checkerboard of nano-cylinders having a height comprised in the range 30-100 nm and a periodicity comprised in the range 35-125 nm. Such nano-cylinders have a diameter comprised in the range 30-100 nm and are arranged orthogonally with respect to the surface of the top 8.

In the third variant of the invention, instead of the nano-cylinders a plasmonic lens is made, or rather a linear chain (self-similar) comprising a plurality of nano-spheres, in particular three, having a diameter comprised in the range 10-100 nm.

Thereafter, some mono-layers of a predetermined material, preferably polytetrafluoroethylene (PTFE—also known as Teflon®, a registered trademark of DuPont), having an overall thickness comprised in the range 1-2 nm are deposed on the microstructures 4.

At this point, after having made the device 1, it is possible to use said device 1 to concentrate and locate a quantity of solute dissolved inside a solution.

FIG. 2 illustrates a flow diagram of the operations to perform according to an embodiment of the invention.

The first operation 50 is to depose a drop of solution, preferably an inorganic solution or a protein suspension, at room temperature, on a device 1 of the type illustrated above, said drop having a spherical shape with a diameter comprised in the range 100 µm-3 mm. Such a drop positions itself on a group of microstructures 4, for example on an area defined by 50×50 microstructures 4, and remains still, suspended on the microstructures 4, thanks to the high contact angle existing between the drop and the microstructures 4 themselves. Preferably, such a contact angle is comprised in the range 160°-170°. Thanks to the presence of mono-layers of Teflon, the contact angle at the solution—micro-structures—air interface is thus increased with respect to the value which it would have without such monolayers.

In step 55 a predetermined length of time should be waited, for example 20 minutes; in such a length of time the solvent of the drop evaporates and the drop reduces in size maintaining its spherical shape. After the solvent has evaporated the drop reduces in size without however leaving solute residue on the microstructures 4, which it abandons due to its size reduction.

Moreover, the drop remains suspended on the microstructures 4 without penetrating between them, thanks to the high contact angle.

In step 60 the evaporation step is repeated thus progressively reducing the size of the drop, up until, for example, the drop has a diameter equal to 40 µm, maintaining the quantity of solute initially present in the drop unaltered but increasing its concentration by up to ten thousand times.

Such a drop with reduced diameter is deposed on a lower number of lithographic micro-structures 4, for example on four or eight microstructures 4, on an area 10 equal, for example, to 20 µm².

When the drop reaches a predetermined minimum radius, for example equal to 40 µm, it collapses (step 65), or rather it spreads evenly upon the lithographic microstructures 4 of the area 10.

Thanks to this progressive reduction process of the size of the drop without losing solute, a solute concentration is obtained with respect to the initial drop, in particular a concentration equal to ten thousand times more. Moreover, the solute is located in a predetermined and very small area 10 of the device.

In step 70 the solute is detected, by scanning, for example, the area 10 with a Raman or fluorescent microscope. The area 10 is illuminated with a microscope which sends a beam of laser light having a predetermined electric field towards said area 10 and the light reflected by the area 10 of the device 1 is analysed through diffraction gratings obtaining a reflection spectrum. By performing a spectroscopic analysis of the reflection spectrum the solute present in the drop is detected.

The corrugated film of gold or silver or the nano-structures made on the top 8 of the lithographic microstructures 4 in the area 10 amplify the local electric field, which then becomes greater than the electric field of the incident light, forming surface plasmons. In this way a very high detection sensitivity is reached, in particular even a single molecule of solute can be detected.

Alternatively, such a solute is a polluting chemical agent, for example a dioxin, and the device 1 according to an embodiment the invention is made on a packaging film. It is therefore possible to exploit the device 1 to detect, performing the aforementioned concentration and locating procedure operations, the presence of polluting substances on the packaging of food products, clothing items, etc.

Clearly, the principle of the invention remaining the same, the embodiments and the constructive details can be widely varied with respect to what has been described and illustrated purely as an example and not for limiting purposes, without for this reason departing from the scope of protection of the present invention defined by the attached claims.

The invention claimed is:

1. A solute concentrator and locator device, the device comprising:
    a substrate;
    a plurality of prismatic lithographic microstructures orthogonally emerging from the substrate, said lithographic microstructures being spaced from one another by a predetermined distance,
    one or more nanometric formations comprising one or more noble metal, said one or more nanometric formations creating one or more uneven surfaces on top of at least some of the lithographic microstructures;
    one or more layers hydrophobic material, said one or more layers hydrophobic material coating at least some of the lithographic microstructures and nanometric formations.

2. The device according to claim 1, wherein said nanometric formations comprise a corrugated continuous film.

3. The device according to claim 1, wherein said nanometric formations comprise a plurality of nanocylinders placed orthogonally to the surface of said top.

4. The device according to claim 1, wherein said nanometric formations comprise a plurality of nanospheres.

5. The device according to claim 1, wherein said nanometric formations have a periodic configuration on the tops of the microstructures.

6. The device according to claim 1, wherein said prismatic lithographic microstructures have the shape of a parallelepiped.

7. The device according to claim 1, wherein the predetermined distance between the microstructures comprises 20-50 µm.

8. A method for making a solute concentrator and locator device of a solute comprising the steps of:
    creating a plurality of prismatic lithographic microstructures on a substrate, said plurality of prismatic lithographic microstructures emerging orthogonally from the substrate and being spaced from one another by a predetermined distance
    forming uneven nanometric formations comprising a noble metal on top surface of at least some of lithographic microstructures; and
    coating said nanometric formations and prismatic lithographic microstructures with one or more layers of hydrophobic material.

9. The method according to claim 8, wherein the step of forming uneven nanometric formations comprises the step of:
    performing an electroless deposition of said noble metal on the top of each microstructure;
    and the step of coating said nanometric formations comprises the step of:
    depositing a plurality of mono-layers of said hydrophobic material.

10. The method according to claim 8, wherein the step of forming uneven nanometric formations comprises the step of:
    Performing an electron beam lithography at high resolution and an electroless deposition of said noble metal on the top surface of each microstructure; and the step of coating said nanometric formations comprises the step of:
    depositing a plurality of monolayers of said hydrophobic material.

11. A method for concentrating and locating a solute by a device comprising the steps of:
    a) providing a substrate;
    b) providing a plurality of prismatic lithographic microstructures orthogonally emerging from the substrate and being spaced from one another by a predetermined distance;
    c) providing, on a top of each respective microstructure, nanometric formations arranged to make uneven a surface of said top, said nanometric formations being of a noble metal;

d) coating said prismatic lithographic microstructures and nanometric formations with a plurality of mono-layers of hydrophobic material;
e) depositing on said device a drop of a solution containing a solute to concentrate and locate that is dissolved in a solvent;
f) waiting for a predetermined length of time so that the drop evaporates partially, whereby the drop reduces in size maintaining its spherical shape and a concentration of the solute increases, so that after the solvent has evaporated the drop reduces in size without leaving solute residue on the microstructures;
g) repeating step f until the drop reaches a minimum predetermined volume occupying a predetermined area on said device;
h) illuminating the predetermined area occupied by the drop with an incident light beam having a predetermined electric field; and
i) analyzing light reflected from the area to reveal the solute present within the solution, said reflected light having an electric field greater than the electric field of the incident light due to said nanometric formations.

12. The method according to claim 11, wherein the analyzing comprises performing a spectroscopic analysis of a reflection spectrum of said reflected light.

13. The method according to claim 11, wherein the step of forming uneven nanometric formations comprises performing an electroless deposition of a noble metal on the top of each microstructure to create a continuous corrugated film, wherein the noble metal comprises silver or gold.

14. The device method according to claim 11, wherein said nanometric formations comprise a plurality of nanocylinders placed orthogonally to the surface of said top and wherein said nanocylinders have a height of approximately 30-100 nm and a diameter of approximately 30-100 nm and are spaced from one another by approximately 35-125 nm.

15. The device method according to claim 11, wherein said nanometric formations comprise a plurality of nanospheres and wherein said nanospheres have a diameter of approximately 10-100 nm.

16. The method according to claim 11, wherein the step of providing the nanometric formations comprises the step of:
performing an electroless deposition of a noble metal on the top of each microstructure; and
depositing a plurality of mono-layers of said hydrophobic material, said hydrophobic material comprising polytetrafluoroethylene.

17. The method according to claim 11, the step of obtaining the nanometric formations comprises the steps of:
performing, in a coordinate manner, an electron beam lithography at high resolution and an electroless deposition of a noble metal on the top of each microstructure; and
depositing a plurality of monolayers of said hydrophobic material, said hydrophobic material comprising polytetrafluoroethylene.

\* \* \* \* \*